United States Patent
Kim et al.

(10) Patent No.: US 10,231,842 B2
(45) Date of Patent: Mar. 19, 2019

(54) INTERVERTEBRAL TENSIONAL ARTIFICIAL DISC REPLACEMENT

(71) Applicants: Solco Biomedical Co., Ltd., Pyeongtaek-Si (KR); Hyeun-Sung Kim, Daejeon (KR)

(72) Inventors: Hyeun-Sung Kim, Daejeon (KR); Hong-Won Yoon, Kunpo-Shi (KR)

(73) Assignees: Solco Biomedical Co., Ltd. (KR); Hyeun-Sung Kim (KR)

( * ) Notice: Subject to any disclaimer, the term of this patent is extended or adjusted under 35 U.S.C. 154(b) by 448 days.

(21) Appl. No.: 15/182,664

(22) Filed: Jun. 15, 2016

(65) Prior Publication Data
US 2016/0296338 A1 Oct. 13, 2016

Related U.S. Application Data

(63) Continuation of application No. PCT/KR2014/008913, filed on Sep. 24, 2014.

(30) Foreign Application Priority Data
Dec. 18, 2013 (KR) .......................... 10-2013-0158545

(51) Int. Cl.
*A61F 2/44* (2006.01)
*A61B 17/70* (2006.01)
(Continued)

(52) U.S. Cl.
CPC ............ *A61F 2/4425* (2013.01); *A61B 17/70* (2013.01); *A61F 2/44* (2013.01); *A61F 2/442* (2013.01);
(Continued)

(58) Field of Classification Search
CPC ................................. A61F 2/4425; A61F 2/442
See application file for complete search history.

(56) References Cited

U.S. PATENT DOCUMENTS

| 4,759,769 A * | 7/1988 | Hedman ............... A61F 2/4425 623/17.13 |
| 5,314,477 A * | 5/1994 | Marnay ................ A61F 2/4425 403/112 |
| 6,682,562 B2 * | 1/2004 | Viart .................... A61F 2/4425 623/17.14 |

FOREIGN PATENT DOCUMENTS

| KR | 10-2005-0112108 A | 11/2005 |
| KR | 10-0948420 B1 | 3/2010 |

(Continued)

OTHER PUBLICATIONS

International Search Report for PCT/KR2014/008913, dated Oct. 31, 2014.

*Primary Examiner* — Christian A Sevilla
(74) *Attorney, Agent, or Firm* — Banner & Witcoff, Ltd.

(57) ABSTRACT

Disclosed herein is an intervertebral tensional artificial disc replacement, insertable between adjacent vertebrae, which includes an inferior plate engaging with a lower vertebra and providing elastic force to an upper vertebra, and a superior plate seated on an upper portion of the inferior plate to engage with the upper vertebra, the superior plate being rotatable right and left within a certain angular range depending on rotation of the upper vertebra. Since the adjacent vertebrae are supported by elastic force, it is possible to prevent abrasion due to frequent friction between upper and lower bodies of the artificial disc replacement. In addition, the intervertebral artificial disc replacement can engage well with a spine and move well by locating the central axis of motion of the intervertebral artificial disc replacement at a rearward position, similar to the central axis of the body's spinal motion.

10 Claims, 8 Drawing Sheets

(51) Int. Cl.
*A61F 2/30* (2006.01)
*A61F 2/46* (2006.01)

(52) U.S. Cl.
CPC ... *A61F 2/4611* (2013.01); *A61F 2002/30001* (2013.01); *A61F 2002/30131* (2013.01); *A61F 2002/30299* (2013.01); *A61F 2002/30563* (2013.01); *A61F 2002/30604* (2013.01); *A61F 2002/30624* (2013.01); *A61F 2002/30649* (2013.01); *A61F 2002/30884* (2013.01); *A61F 2002/30904* (2013.01); *A61F 2002/443* (2013.01)

(56) References Cited

FOREIGN PATENT DOCUMENTS

KR 10-2011-0003540 A 1/2011
KR 10-1087153 B1 11/2011

\* cited by examiner

FLEXTION / EXTENSION

CENTRAL AXIS OF CERVICAL MOTION

CENTRAL AXIS OF CERVICAL MOTION

INTERVERTEBRAL TENSIONAL ARTIFICIAL DISC REPLACEMENT

CROSS-REFERENCE TO RELATED APPLICATION

This application claims the priority benefit of Korean Patent Application No. 10-2013-0158545, filed on Dec. 18, 2013 in the Korean Intellectual Property Office, the disclosure of which is incorporated herein by reference.

BACKGROUND OF THE INVENTION

1. Field of the Invention

The present invention relates to an intervertebral artificial disc replacement, and more particularly to an intervertebral tensional artificial disc replacement which is implanted to replace a damaged disc between vertebrae.

2. Description of the Related Art

A disc is between vertebrae, the outside of the disc is protected by tough fiber, and a nucleus pulposus is present inside the disc.

The disc functions as a joint, and plays a very important role in reducing an impact applied to a spine by changing the position and form of the nucleus pulposus according to the movement of the spine. The nucleus pulposus consists mostly of moisture (water), and the disc loses its buffering function as humans grow old and the amount of moisture is gradually reduced. For this reason, backaches occur when excessive pressure is applied to the fiber, and if this state worsens, the fiber presses posterior nerve roots while being greatly stretched or ruptured, thereby causing pain in the pelvis, legs, etc. Then, a variety of side effects such as vertebral deformation occur while the gap between vertebrae is gradually narrowed or the vertebrae move down. Accordingly, when a surgical operation is performed to remove discs which are badly bent or damaged, it is basically necessary to take measures for maintaining the gap between vertebrae and preventing the vertebrae from being deformed or rocked.

Conventionally, spinal fusion is mainly performed to fix vertebrae using titanium screws or the like while maintaining the normal gap between the vertebrae. However, the conventional medical procedures may cause side effects such as backaches due to the fixed vertebrae.

Accordingly, artificial disc replacements (ADRs) have been recently developed and are being well received by patients. Artificial disc replacement is a surgical method for treating discs without fixing a vertebral body. Even after the surgical operation, the artificial disc replacement implanted by the surgical operation is similar to the disc of a human body in terms of mobility, flexibility, and safety of vertebral segments, and side effects such as backaches due to the conventional spinal fusion do not occur.

In connection with such a recent artificial disc replacement, the artificial disc replacement includes an upper fixed body, a lower fixed body, and an intermediate connection body which is inserted therebetween to connect the upper and lower fixed bodies. Since the upper fixed body moves depending on the movement of vertebrae in the state in which the upper fixed body is in contact with the intermediate connection body, there is a problem in that the intermediate connection body and the upper fixed body become worn due to friction when used for a long period, and foreign substances may be generated in a human body. In addition, since the upper fixed body and the intermediate connection body must be made of special materials in order to prevent the generation of foreign substances, high expense is incurred.

SUMMARY OF THE INVENTION

Therefore, the present invention has been made in view of the above problems, and it is an object of the present invention to provide an intervertebral tensional artificial disc replacement capable of being inserted between adjacent vertebrae and supporting the vertebrae by elastic force, thereby preventing abrasion due to frequent friction between upper and lower bodies of the artificial disc replacement.

It is another object of the present invention to provide an intervertebral tensional artificial disc replacement capable of engaging well with a spine and moving well by locating the central axis of motion of the intervertebral artificial disc replacement at a rearward position, similar to the central axis of the body's spinal motion, the central axis of the body's spinal motion being located beyond a vertebral body (located within a range of about ⅓ from the rear of the vertebral body) in terms of medicine.

In accordance with the present invention, the above and other objects can be accomplished by the provision of an intervertebral tensional artificial disc replacement, insertable between adjacent vertebrae, which includes an inferior plate engaging with a lower vertebra and providing elastic force to an upper vertebra, and a superior plate seated on an upper portion of the inferior plate to engage with the upper vertebra, the superior plate being rotatable right and left within a certain angular range depending on rotation of the upper vertebra.

The inferior plate may have a "ㄴ" shape, and when a front portion of the upper vertebra is moved downward, an upper end of the "ㄴ"-shaped inferior plate may be moved downward by a load of the upper vertebra.

The "ㄷ"-shaped inferior plate may have an opening portion formed on an upper end thereof, and the superior plate may be coupled to and seated on the opening portion.

The inferior plate may include a lower vertebra support part engaging with the lower vertebra to prevent the intervertebral tensional artificial disc replacement from being separated therefrom, a seating part having a structure corresponding to a lower surface of the superior plate so that the superior plate is rotatably seated on the seating part, and an elastic connection part configured to connect the lower vertebra support part and the seating part, the elastic connection part providing elastic force to the seating part folded in response to downward movement of a front portion of the upper vertebra.

The seating part may be divided into two left and right parts consisting of a first seating part and a second seating part, and each of the first and second seating parts may include a concave rotation guide part such that the lower surface of the superior plate is rotatably coupled thereto.

The elastic connection part may have a circular shape so as to be easily bent and provide elastic force.

The elastic connection part may have a groove having a predetermined length and formed in a center thereof, so that one portion of the elastic connection part connected to the first seating part is bent by a load applied to the first seating part and the other portion of the elastic connection part connected to the second seating part is bent by a load applied to the second seating part.

The elastic connection part may have grooves formed to the left and the right thereof, each having a predetermined length, so that the elastic connection part is easily bent in a corresponding direction by a load applied to the first or second seating part.

The superior plate may include an upper vertebra support part engaging with the upper vertebra to prevent the intervertebral tensional artificial disc replacement from being separated therefrom, and a circular rotation part provided on a lower surface of the upper vertebra support part, and rotatably coupled to an upper surface of the inferior plate.

The circular rotation part may have prevention bumps formed in the front and rear thereof in order to prevent the circular rotation part from rotating at an angle equal to or greater than a certain angle, and the circular rotation part may be prevented from rotating at an angle equal to or greater than the certain angle by catching of the prevention bumps in the inferior plate.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION OF THE PREFERRED EMBODIMENTS

Reference will now be made in detail to the preferred embodiments of the present invention, examples of which are illustrated in the accompanying drawings.

Figure 1:
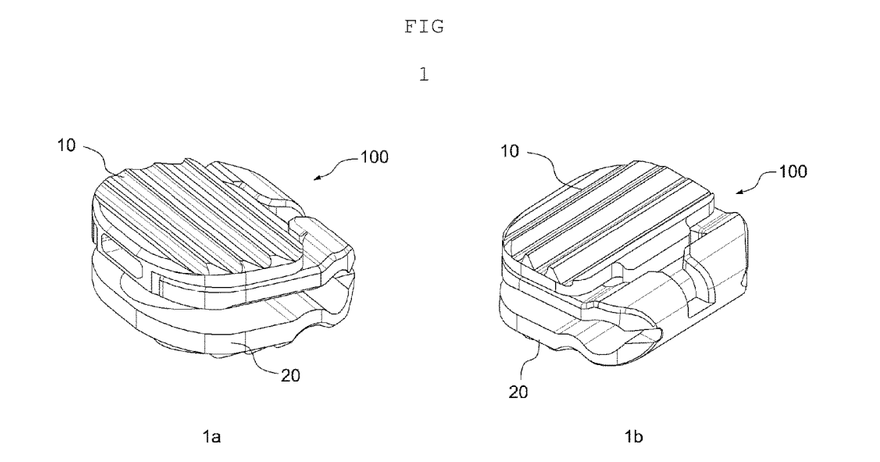
FIG. 1 is a perspective view illustrating an intervertebral tensional artificial disc replacement according to an embodiment of the present invention.
Figure 2:
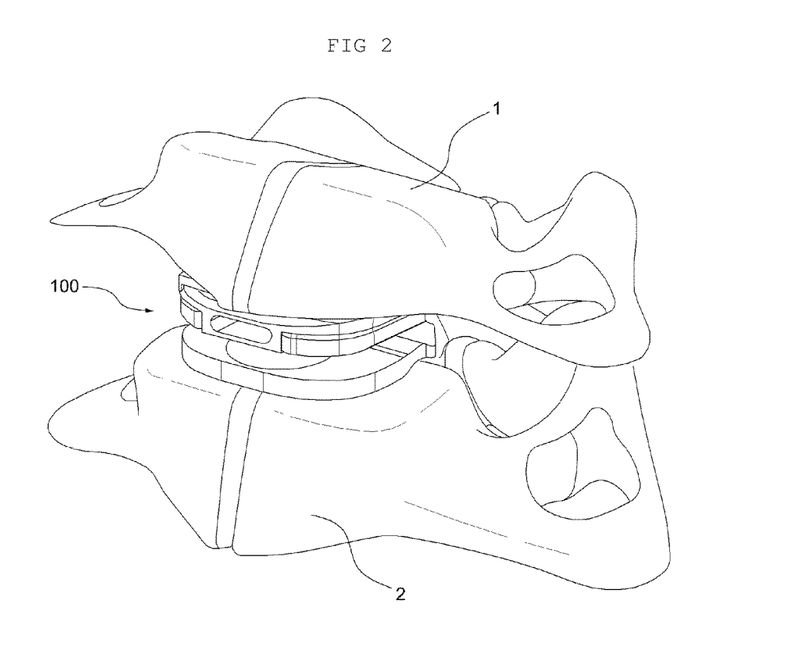
FIG. 2 is a perspective view illustrating a state in which the intervertebral tensional artificial disc replacement according to the embodiment of the present invention is inserted between cervical vertebrae.

FIG. 1 is a perspective view illustrating an intervertebral tensional artificial disc replacement according to an embodiment of the present invention. FIG. 2 is a perspective view illustrating a state in which the intervertebral tensional artificial disc replacement according to the embodiment of the present invention is inserted between cervical vertebrae.

Referring to FIG. 1, the intervertebral tensional artificial disc replacement, which is designated by reference numeral 100, includes an inferior plate 20 and a superior plate 10.

When a disc constituting cervical vertebrae (neck bones) or lumbar vertebrae (haunch bones) is damaged, the intervertebral tensional artificial disc replacement 100 is inserted between adjacent vertebrae constituting the cervical vertebrae or the lumbar vertebrae, in order to replace the disc.

FIG. 2 illustrates that the intervertebral tensional artificial disc replacement 100 is inserted between an upper vertebra 1 and a lower vertebra 2 which constitute the cervical vertebrae.

The inferior plate 20 engages with the lower vertebra 2 and provides elastic force to the upper vertebra 1.

The superior plate 10 is seated on the upper portion of the inferior plate 20 to engage with the upper vertebra 1, and is rotatable right and left within a certain angular range depending on the rotation of the upper vertebra 1.

The inferior plate 20 acts as a buffer by providing elastic force when the adjacent vertebrae constituting the cervical vertebrae are vertically moved about the central axes thereof. Since the superior plate 10 engages with the upper vertebra 1, the superior plate 10 rotates right and left within a certain angular range depending on the right and left rotation of the upper vertebra 1 in the state in which the inferior plate 20 is not moved.

Figure 3:
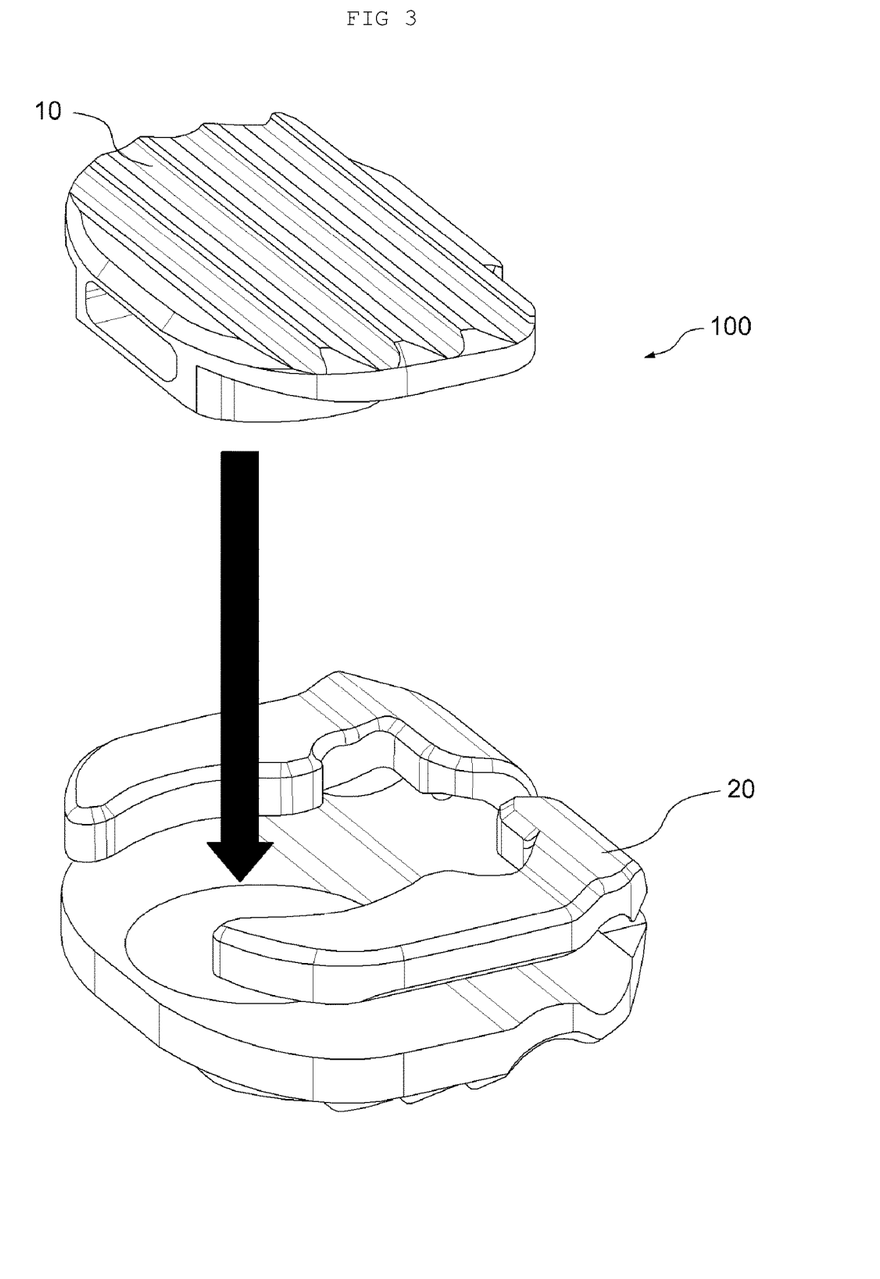
FIG. 3 is a perspective view illustrating a method of coupling a superior plate to an inferior plate in the intervertebral tensional artificial disc replacement according to the embodiment of the present invention.

FIG. 3 is a perspective view illustrating a method of coupling the superior plate to the inferior plate in the intervertebral tensional artificial disc replacement according to the embodiment of the present invention.

Referring to FIG. 3, the superior plate 10 is coupled from top to bottom to an opening portion formed on the upper portion of the inferior plate 20 so as to be seated on the inferior plate 20.

Specifically, the inferior plate 20 may have a "⊏" shape when viewed from the side, the opening portion may be formed on the upper end of the "⊏"-shaped inferior plate, and the superior plate may be coupled to the opening portion. When the front portion of the upper vertebra 1 is moved downward, the upper end of the "⊏"-shaped inferior plate is moved downward by the load of the upper vertebra, but the upper vertebra 1 is supported by the elastic force provided to the upper vertebra 1 by the inferior plate 20 (see FIG. 12).

The configuration of the superior and inferior plates 10 and 20 will be described below in detail.

Figure 4:
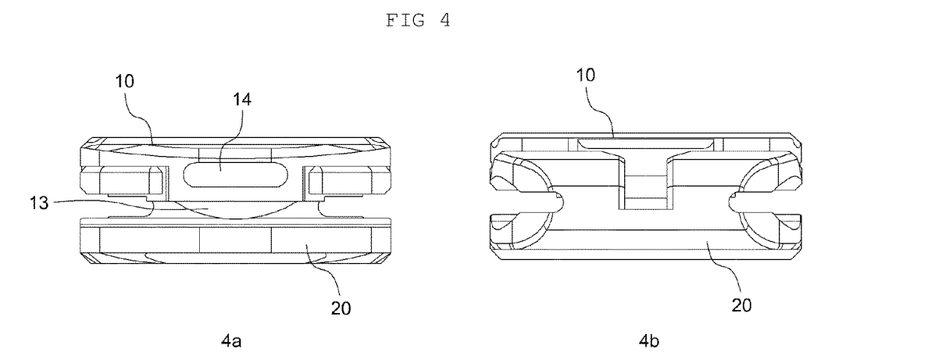
FIG. 4 is front and back views illustrating the intervertebral tensional artificial disc replacement according to the embodiment of the present invention.
Figure 5:
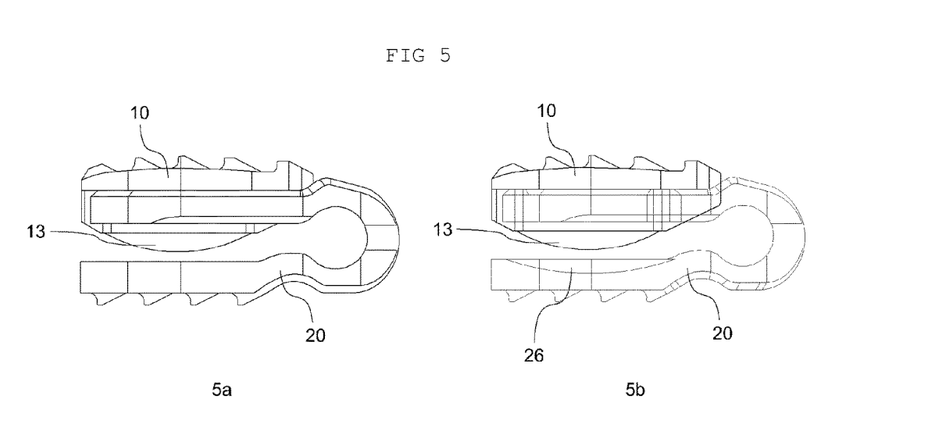
FIG. 5 is side and side projection views illustrating the intervertebral tensional artificial disc replacement according to the embodiment of the present invention.

FIG. 4 is front and back views illustrating the intervertebral tensional artificial disc replacement according to the embodiment of the present invention. FIG. 5 is side and side projection views illustrating the intervertebral tensional artificial disc replacement according to the embodiment of the present invention.

Referring to FIGS. 4 and 5, the intervertebral tensional artificial disc replacement 100 includes the superior plate 10 and the inferior plate 20. An instrument-holding groove 14 is formed in front of the lower portion of the superior plate 10, such that an instrument for the insertion of the intervertebral tensional artificial disc replacement 100 between the adjacent vertebrae may be inserted into the instrument-holding groove 14. A convex curved part 13 is formed beneath the instrument-holding groove 14.

When the intervertebral tensional artificial disc replacement 100 is viewed from the front and the side, it may be seen that the convex curved part 13 is spaced apart from the bottom of the inferior plate 20 by a predetermined distance.

A concave curved part 26 is formed in the bottom of the "ㄴ"-shaped inferior plate 20, and has a shape corresponding to the convex curved part 13 formed in the lower portion of the superior plate 10. When a large load is applied to the upper end of the "ㄷ"-shaped inferior plate from the upper vertebra 1, the concave curved part 26 comes into contact with the convex curved part 13. The concave curved part 26 does not always come into contact with the convex curved part 13 when a load is applied thereto from the upper vertebra 1. For example, when a small load is applied to the inferior plate, a gap may be formed between the concave curved part 26 and the convex curved part 13 by the elastic force.

Figure 6:
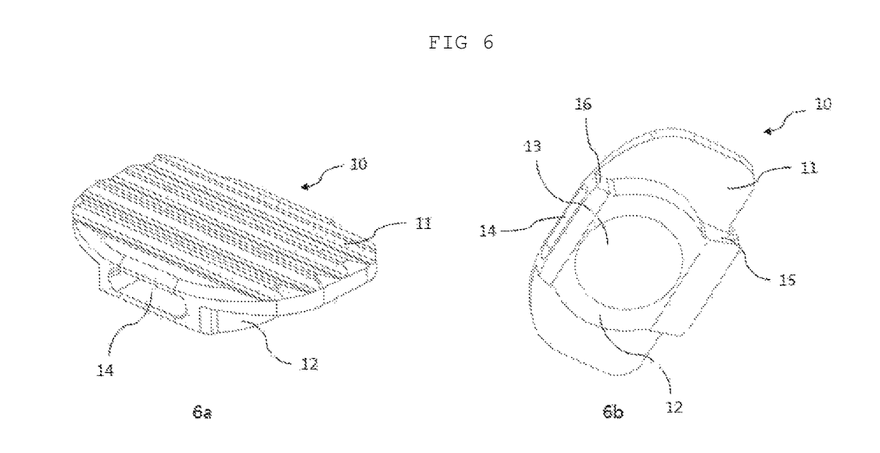
FIG. 6 is a perspective view illustrating a superior plate.
Figure 7:
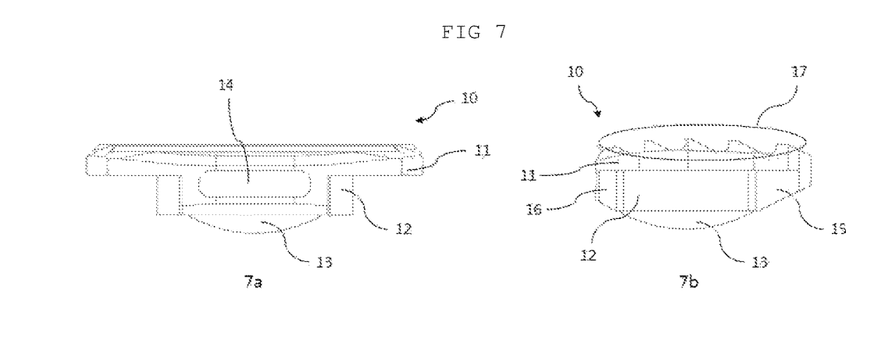
FIG. 7 is front and side views illustrating the superior plate.
Figure 13:
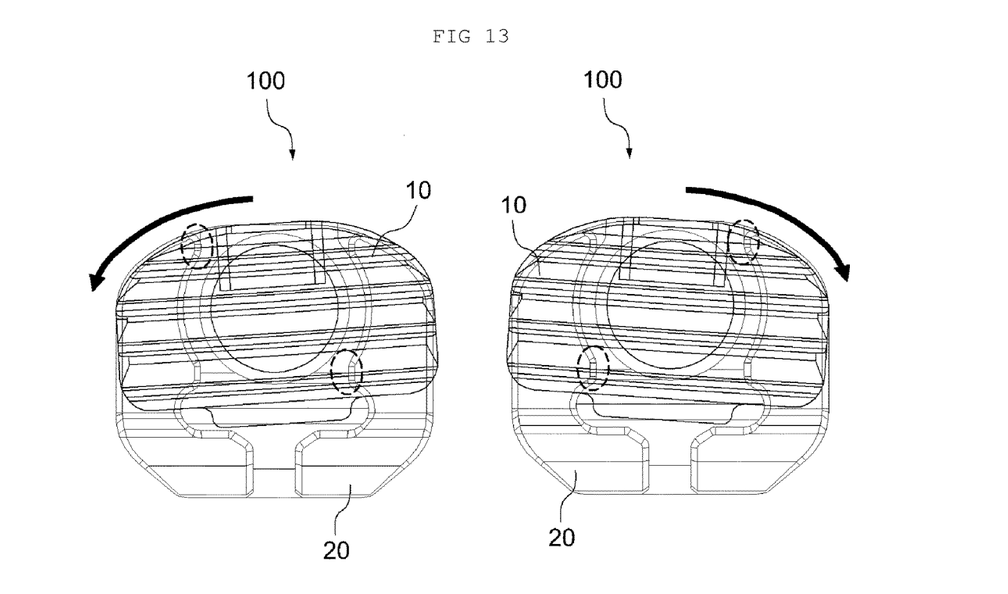
FIG. 13 is a view illustrating an exemplary state in which, when the superior plate rotates right and left, the superior plate rotates only within a certain angular range owing to prevention bumps.

FIG. 6 is a perspective view illustrating the superior plate. FIG. 7 is front and side views illustrating the superior plate. FIG. 13 is a view illustrating an exemplary state in which, when the superior plate rotates right and left, the superior plate rotates only within a certain angular range owing to prevention bumps.

Referring to FIGS. 6 and 7, the superior plate 10 includes an upper vertebra support part 11 and a circular rotation part 12.

The upper vertebra support part 11 engages with the upper vertebra 1 to prevent the intervertebral tensional artificial disc replacement 100 from being separated therefrom. Specifically, the upper vertebra support part 11 has a plurality of toothed fixing protrusions 17 formed on the upper surface thereof so that the toothed fixing protrusions 17 engage with the upper vertebra 1.

The circular rotation part 12 is provided on the lower surface of the upper vertebra support part 11, and is coupled to the upper surface of the inferior plate 20 so as to be rotatable.

The convex curved part 13 is formed beneath the circular rotation part 12 so as to come into contact with the concave curved part 26 formed in the bottom of the inferior plate 20 when the circular rotation part 12 is folded by the load of the upper vertebra 1 due to the vertical movement thereof.

When the superior plate 10 moves downward by the load applied thereto, the convex curved part 13 formed beneath the circular rotation part 12 comes into contact with the concave curved part 26 formed in the bottom of the inferior plate 20, thereby preventing the edge portion of the superior plate 10 from coming into contact with the edge portion of the inferior plate 20. Thereby, it is possible to prevent abrasion between the edge portions of the superior and inferior plates 10 and 20.

The circular rotation part 12 has prevention bumps 16 and 15 formed in the front and rear thereof in order to prevent the circular rotation part 12 from rotating at an angle equal to or greater than a certain angle. Thus, the circular rotation part 12 is prevented from rotating at an angle equal to or greater than the certain angle by catching of the prevention bumps 16 and 15 in the inferior plate 20.

Referring to FIG. 13, it may be seen that the superior plate 10 seated on the inferior plate 20 is not rotated right and left any further due to the front and rear prevention bumps 16 and 15. As such, by limiting the rotation of the superior plate within a certain angle using the prevention bumps 16 and 15, an artificial disc replacement substantially similar to the disc between the vertebrae of the cervical vertebrae or the lumbar vertebrae may be embodied.

The instrument-holding groove 14 is provided in front of the circular rotation part 12 such that the instrument for the insertion of the intervertebral tensional artificial disc replacement 100 between the adjacent vertebrae 1 and 2 may be inserted into the instrument-holding groove 14. After the instrument is inserted into the instrument-holding groove 14 in the state in which the superior plate 10 is coupled to the inferior plate 20, the intervertebral tensional artificial disc replacement 100 is inserted between the adjacent vertebrae.

Figure 8:
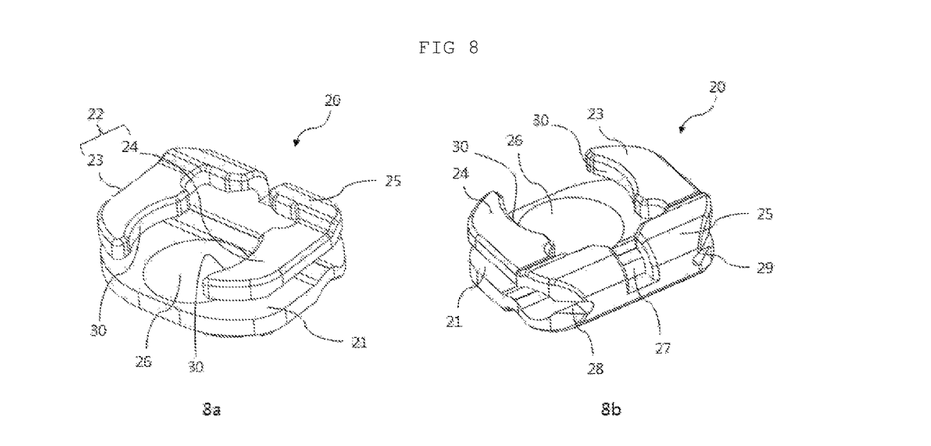
FIG. 8 is a perspective view illustrating an inferior plate.
Figure 9:
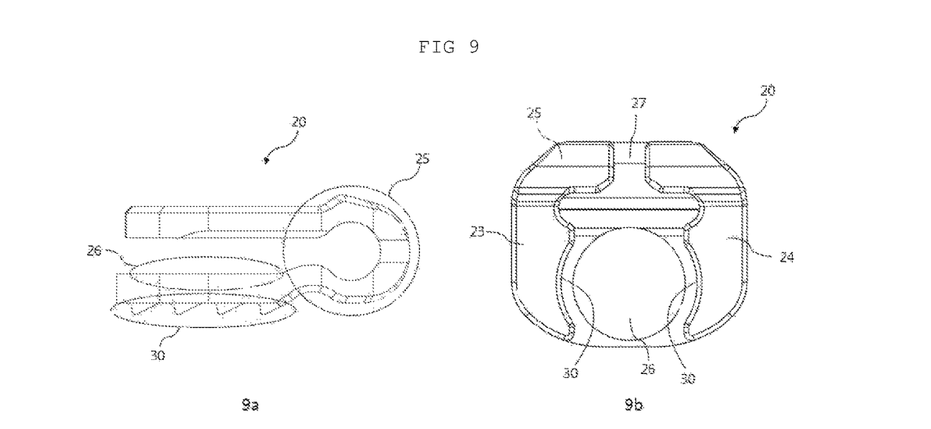
FIG. 9 is side and top views illustrating the inferior plate.
Figure 10:
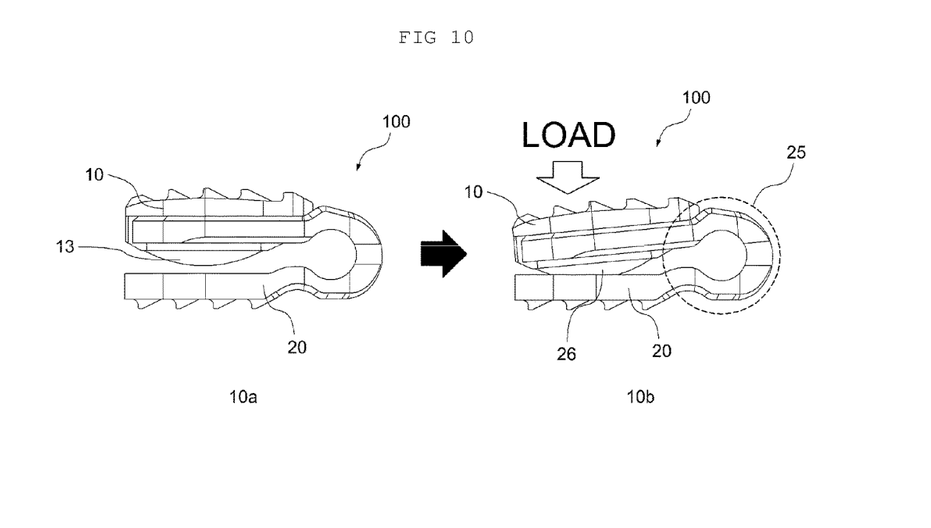
FIG. 10 is a view illustrating an exemplary state in which, when a load is applied from an upper vertebra to the intervertebral tensional artificial disc replacement according to the embodiment of the present invention, the superior plate moves downward while an elastic connection part is bent.
Figure 11:
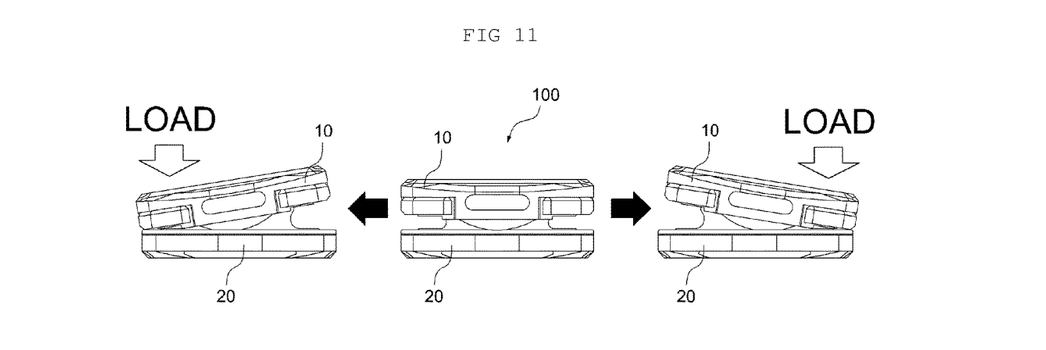
FIG. 11 is a view illustrating an exemplary state in which, when a load is applied to the left or the right of the intervertebral tensional artificial disc replacement according to the embodiment of the present invention, the superior plate moves left or right depending on the direction of the load applied thereto.

FIG. 8 is a perspective view illustrating the inferior plate. FIG. 9 is side and top views illustrating the inferior plate. FIG. 10 is a view illustrating an exemplary state in which, when a load is applied from the upper vertebra to the intervertebral tensional artificial disc replacement according to the embodiment of the present invention, the superior plate comes into contact with the inferior plate. FIG. 11 is a view illustrating an exemplary state in which, when a load is applied to the left or the right of the intervertebral tensional artificial disc replacement according to the embodiment of the present invention, the superior plate is folded.

Referring to FIGS. 8 and 9, the inferior plate 20 includes a lower vertebra support part 21, a seating part 22, and an elastic connection part 25.

The lower vertebra support part 21 engages with the lower vertebra 2 to prevent the intervertebral tensional artificial disc replacement 100 from being separated therefrom. Specifically, the lower vertebra support part 21 has a plurality of toothed fixing protrusions 30 formed on the lower surface thereof so that the toothed fixing protrusions 30 engage with the lower vertebra 2.

The seating part 22 has a structure corresponding to the lower surface of the superior plate 10, and the superior plate 10 is seated on the seating part 22 to be rotatable. The opening portion is formed in the center of the seating part 22, and the lower portion of the superior plate 10 is coupled to the opening portion.

Specifically, the seating part 22 is divided into two left and right parts, i.e. a first seating part 23 and a second seating part 24. Each of the first and second seating parts 23 and 24 includes a concave rotation guide part 30 such that the lower surface of the superior plate 10 is rotatably coupled thereto. The upper vertebra support part 11 of the superior plate 10 is seated on the first and second seating parts 23 and 24, and the circular rotation part 12 is coupled to the concave rotation guide part 30 so as to rotate right and left within a certain angular range.

The elastic connection part 25 connects the lower vertebra support part 21 to the seating part 22, and provides elastic force to the seating part 22 which is folded in response to the downward movement of the front portion of the upper vertebra 1.

Preferably, the elastic connection part 25 has a circular shape so as to be easily bent and provide elastic force.

The elastic connection part 25 has a groove 27 which has a predetermined length and is formed in the center thereof, so that one portion of the elastic connection part 25 connected to the first seating part 23 is bent by the load applied to the first seating part 23 and the other portion of the elastic connection part 25 connected to the second seating part 24 is bent by the load applied to the second seating part 24. Thus, the elastic connection part 25 may be more flexibly moved by the groove 27, formed in the center thereof, depending on the direction of the load applied thereto.

The elastic connection part 25 has grooves 28 and 29 which each have a predetermined length and are formed to the left and the right thereof, so that the elastic connection part 25 is easily bent in a corresponding direction by the load applied to the first or second seating part 23 or 24. When a load is applied to the first seating part 23, the elastic connection part 25 may be more easily bent toward the first seating part 23 by the groove 29 formed toward the first seating part 23. In addition, when a load is applied to the second seating part 24, the elastic connection part 25 may be more easily bent toward the second seating part 24 by the groove 28 formed toward the second seating part 24.

Referring to FIG. 10, it may be seen that the "⊏"-shaped inferior plate 20 is folded downward by the load applied to the superior plate 10, which engages with the upper vertebra 1, depending on the vertical movement of the upper vertebra 1. In this case, the elastic connection part 25 provides elastic force in the direction of the upper vertebra 1 while bending.

In addition, when a large load is applied to the superior plate from the upper vertebra 1, the convex curved part 13 formed on the superior plate 10 may come into contact with the concave curved part 26 formed in the bottom of the inferior plate 20.

Referring to FIG. 11, when a load is applied to the left of the superior plate 10, the inferior plate 20 is bent to the left. When a load is applied to the right of the superior plate 10, the inferior plate 20 is bent to the right. That is, the inferior plate is flexibly bent in a corresponding direction by the groove 27 formed in the center of the elastic connection part 25 and the grooves 28 and 29 which each have a predetermined length and are formed to the left and the right thereof.

Figure 12:
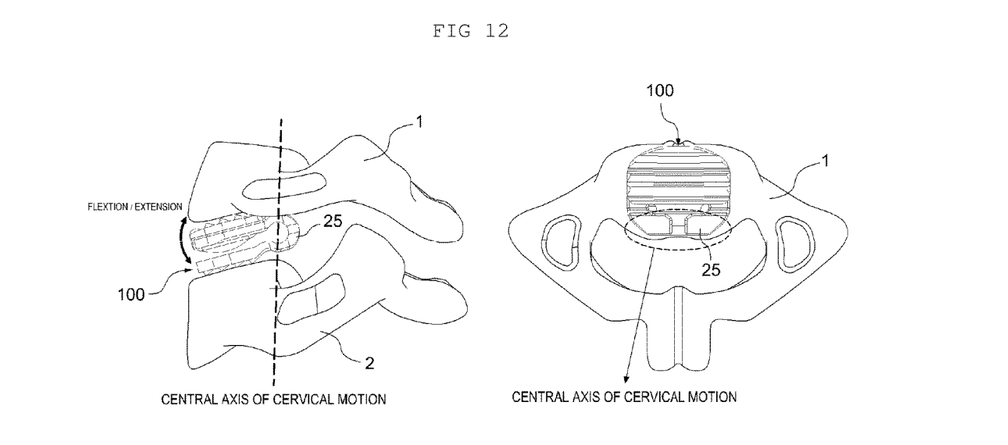
FIG. 12 is a view illustrating an exemplary state in which the intervertebral tensional artificial disc replacement is inserted on the basis of the central axis of cervical motion.

FIG. 12 is a view illustrating an exemplary state in which the intervertebral tensional artificial disc replacement is inserted on the basis of the central axis of cervical motion.

Referring to FIG. 12, the elastic connection part 25 of the inferior plate 20 is located at the central axis of cervical motion so that adjacent vertebrae 1 and 2 are stably supported. The elastic connection part 25 provides elastic force to the adjacent vertebrae 1 and 2, depending on the vertical movement of the upper vertebra 1 about the central axis.

Figure 14:
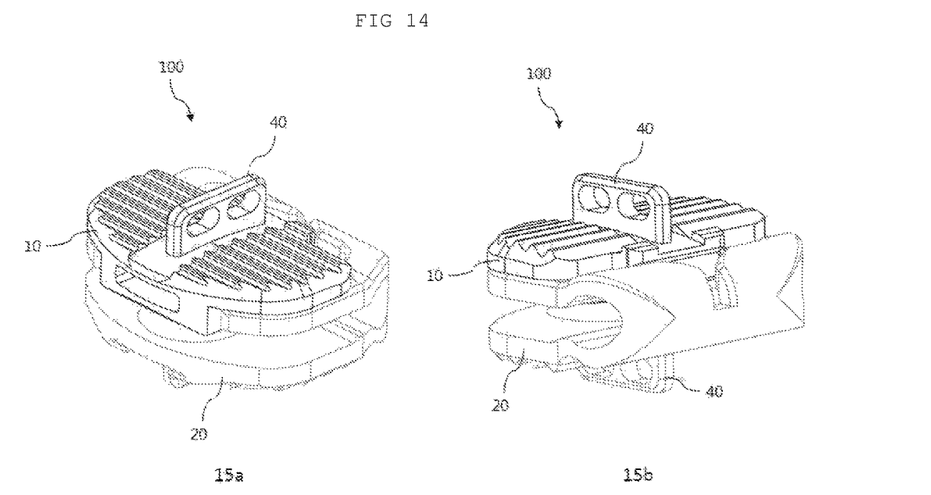
FIG. 14 is a perspective view illustrating an intervertebral tensional artificial disc replacement which is inserted between lumbar vertebrae according to another embodiment of the present invention.
Figure 15:
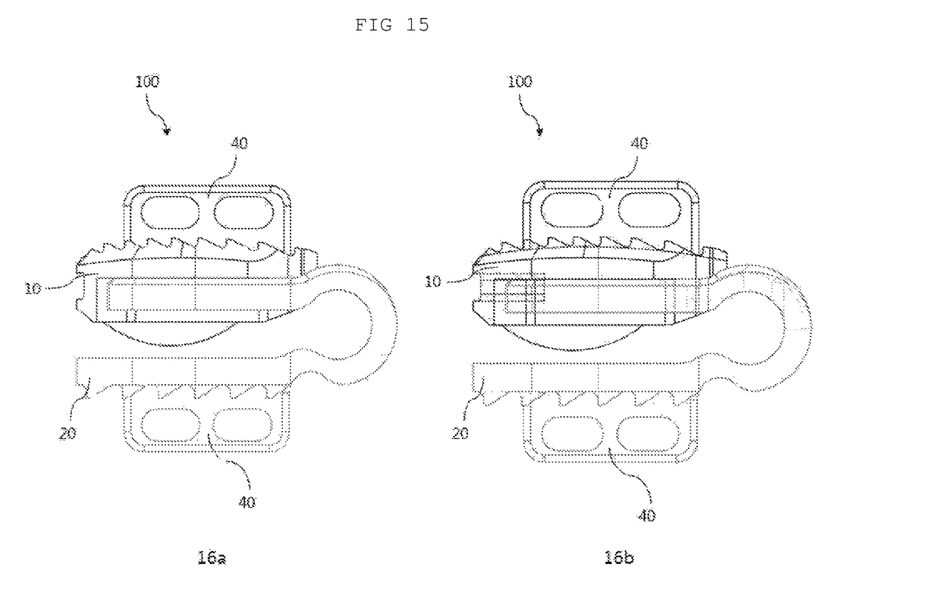
FIG. 15 is side and side projection views illustrating the intervertebral tensional artificial disc replacement which is inserted between the lumbar vertebrae.

FIG. 14 is a perspective view illustrating an intervertebral tensional artificial disc replacement which is inserted between lumbar vertebrae according to another embodiment of the present invention. FIG. 15 is side and side projection views illustrating the intervertebral tensional artificial disc replacement which is inserted between the lumbar vertebrae.

Referring to FIGS. 14 and 15, the basic configuration of the intervertebral tensional artificial disc replacement 100 which is inserted between the lumbar vertebrae is identical to the intervertebral tensional artificial disc replacement 100 which is inserted between the cervical vertebrae as described in the previous embodiment.

However, in the intervertebral tensional artificial disc replacement 100 of the present embodiment, the upper surface of the superior plate 10 and the lower surface of the inferior plate 20 are respectively provided with keels 40 which are vertically formed so as to engage with the adjacent vertebrae. The basic configuration and operation of the intervertebral tensional artificial disc replacement according to the present embodiment are similar to those of the intervertebral tensional artificial disc replacement according to the above embodiment, except for the additional inclusion of the keels 40. The lumbar vertebrae are cut to insert the keels into the upper and lower vertebrae constituting the lumbar vertebrae, and the intervertebral tensional artificial disc replacement is then inserted therebetween.

In accordance with the embodiments of the present invention, since the adjacent vertebrae are supported by the elastic force, it is possible to prevent abrasion due to frequent friction between the upper and lower bodies of the artificial disc replacement.

In addition, since the central axis of the body's spinal motion is located beyond the vertebral body (located within the range of about ⅓ from the rear of the vertebral body) in terms of medicine, the intervertebral artificial disc replacement can engage well with the spine and move well by locating the central axis of motion of the intervertebral artificial disc replacement at a rearward position, similar to the central axis of the body's spinal motion. Thus, it is possible to realize movement of the spine similar to that before the artificial disc replacement was fitted, without any difference in sensation.

In addition, since the superior plate is rotatable right and left, the superior plate can rotate right and left within a certain angular range in response to the rotation of the upper vertebra.

In addition, when the load is applied to the intervertebral artificial disc replacement depending on the downward movement of the upper vertebra, the convex curved part formed in the lower portion of the superior plate can come into contact with the concave curved part formed in the bottom of the inferior plate. Consequently, it is possible to prevent abrasion due to friction of the edge portion of the artificial disc replacement.

As is apparent from the above description, in accordance with an intervertebral tensional artificial disc replacement of the present invention, since adjacent vertebrae are supported by elastic force, it is possible to prevent abrasion due to frequent friction between the upper and lower bodies of the artificial disc replacement.

In addition, since the central axis of the body's spinal motion is located beyond a vertebral body (located within the range of about ⅓ from the rear of the vertebral body) in terms of medicine, the intervertebral artificial disc replacement can engage well with a spine and move well by locating the central axis of motion of the intervertebral artificial disc replacement at a rearward position, similar to the central axis of the body's spinal motion. Thus, it is possible to realize movement of the spine similar to that before the artificial disc replacement was fitted, without any difference in sensation.

In addition, since a superior plate is rotatable right and left, the superior plate can rotate right and left within a certain angular range in response to the rotation of an upper vertebra.

In addition, when a load is applied to the intervertebral artificial disc replacement depending on the downward movement of the upper vertebra, a convex curved part formed in the lower portion of the superior plate can come into contact with a concave curved part formed in the bottom of an inferior plate. Consequently, it is possible to prevent abrasion due to friction of the edge portion of the artificial disc replacement.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. An intervertebral tensional artificial disc replacement, insertable between adjacent vertebrae, comprising:
    an inferior plate configured to engage with a lower vertebra and configured to provide elastic force to an upper vertebra; and
    a superior plate seated on an upper portion of the inferior plate to engage with the upper vertebra, the superior plate being rotatable right and left within a certain angular range depending on rotation of the upper vertebra.

2. The intervertebral tensional artificial disc replacement according to claim 1, wherein the inferior plate has a "⌴" shape, and when a front portion of the upper vertebra is moved downward, an upper end of the "⌴"-shaped inferior plate is moved downward by a load of the upper vertebra.

3. The intervertebral tensional artificial disc replacement according to claim 1, wherein the "⌴"-shaped inferior plate has an opening portion formed on an upper end thereof, and the superior plate is coupled to and seated on the opening portion.

4. The intervertebral tensional artificial disc replacement according to claim 1, wherein the inferior plate comprises:
    a lower vertebra support part configured engage with the lower vertebra to prevent the intervertebral tensional artificial disc replacement from being separated therefrom;
    a seating part having a structure corresponding to a lower surface of the superior plate so that the superior plate is rotatably seated on the seating part; and
    an elastic connection part configured to connect the lower vertebra support part and the seating part, the elastic connection part providing elastic force to the seating part folded in response to downward movement of a front portion of the upper vertebra.

5. The intervertebral tensional artificial disc replacement according to claim 4, wherein the seating part is divided into two left and right parts consisting of a first seating part and a second seating part, and each of the first and second seating parts comprises a concave rotation guide part such that the lower surface of the superior plate is rotatably coupled thereto.

6. The intervertebral tensional artificial disc replacement according to claim 4, wherein the elastic connection part has a circular shape so as to be easily bent and provide elastic force.

7. The intervertebral tensional artificial disc replacement according to claim 5, wherein the elastic connection part has a groove having a predetermined length and formed in a center thereof, so that one portion of the elastic connection part connected to the first seating part is bent by a load applied to the first seating part and the other portion of the elastic connection part connected to the second seating part is bent by a load applied to the second seating part.

8. The intervertebral tensional artificial disc replacement according to claim 5, wherein the elastic connection part has grooves formed to the left and the right thereof, each having a predetermined length, so that the elastic connection part is easily bent in a corresponding direction by a load applied to the first or second seating part.

9. The intervertebral tensional artificial disc replacement according to claim 1, wherein the superior plate comprises:
    an upper vertebra support part engaging with the upper vertebra to prevent the intervertebral tensional artificial disc replacement from being separated therefrom; and
    a circular rotation part provided on a lower surface of the upper vertebra support part, and rotatably coupled to an upper surface of the inferior plate.

10. The intervertebral tensional artificial disc replacement according to claim 9, wherein the circular rotation part has prevention bumps formed in the front and rear thereof in order to prevent the circular rotation part from rotating at an angle equal to or greater than a certain angle, and the circular rotation part is prevented from rotating at an angle equal to or greater than the certain angle by catching of the prevention bumps in the inferior plate.

* * * * *